(12) United States Patent
Whelan

(10) Patent No.: US 10,379,010 B2
(45) Date of Patent: Aug. 13, 2019

(54) SEGMENT SAMPLER

(71) Applicant: NOBLE HOUSE GROUP PTY. LTD., Chelsea Heights, Victoria (AU)

(72) Inventor: Chris Whelan, Leichhardt (AU)

(73) Assignee: NOBLE HOUSE GROUP PTY. LTD. (AU)

( * ) Notice: Subject to any disclaimer, the term of this patent is extended or adjusted under 35 U.S.C. 154(b) by 132 days.

(21) Appl. No.: 15/328,503

(22) PCT Filed: Jul. 24, 2015

(86) PCT No.: PCT/AU2015/000440
§ 371 (c)(1),
(2) Date: Jan. 24, 2017

(87) PCT Pub. No.: WO2016/011492
PCT Pub. Date: Jan. 28, 2016

(65) Prior Publication Data
US 2017/0219462 A1    Aug. 3, 2017

Related U.S. Application Data

(60) Provisional application No. 62/028,411, filed on Jul. 24, 2014.

(51) Int. Cl.
*G01N 1/14* (2006.01)
*G01N 1/10* (2006.01)
(Continued)

(52) U.S. Cl.
CPC ........... *G01N 1/14* (2013.01); *A61B 5/15003* (2013.01); *A61B 5/150534* (2013.01); *A61B 5/150992* (2013.01); *A61B 10/0045* (2013.01); *A61M 1/0236* (2014.02); *B01L 3/0296* (2013.01); *B01L 3/502* (2013.01); *B01L 3/561* (2013.01); *B01L 3/563* (2013.01); *G01N 1/10* (2013.01);
(Continued)

(58) Field of Classification Search
CPC ............................. B01L 3/0296; B01L 3/0293
See application file for complete search history.

(56) References Cited

U.S. PATENT DOCUMENTS 4,176,451 A * 12/1979 McMorrow ........... B01L 3/0293
30/124
4,886,072 A * 12/1989 Percarpio ........... A61B 5/15003
600/576

(Continued)

FOREIGN PATENT DOCUMENTS

DE    19947966    4/2001
EP    0875293     6/2003
EP    0894532     9/2004

*Primary Examiner* — Paul M. West
*Assistant Examiner* — Mark A Shabman
(74) *Attorney, Agent, or Firm* — Galbreath Law Offices, P.C.; John A. Galbreath

(57) ABSTRACT

A tube segment sampler system (10) for withdrawing a fluid sample from a tube segment (100), the sampler (10) having a first tube piercing member (28) for piercing the tube segment at a first location and a second tube piercing member (28) for piercing the tube segment at a second location so as to allow air to be drawn into the tube segment (100) through one of the openings made by one of the piercing members (28) while fluid is withdrawn through the other of the openings.

21 Claims, 14 Drawing Sheets

(51) Int. Cl.
  *A61M 1/02* (2006.01)
  *A61B 10/00* (2006.01)
  *B01L 3/00* (2006.01)
  *G01N 33/49* (2006.01)
  *B01L 3/02* (2006.01)
  *A61B 5/15* (2006.01)
  *G01N 35/10* (2006.01)

(52) U.S. Cl.
  CPC ........ *G01N 33/49* (2013.01); *A61B 5/150213* (2013.01); *A61B 5/150389* (2013.01); *A61B 5/150503* (2013.01); *B01L 2200/026* (2013.01); *B01L 2300/0672* (2013.01); *B01L 2300/0832* (2013.01); *B01L 2300/0848* (2013.01); *B01L 2400/0478* (2013.01); *G01N 35/1079* (2013.01); *G01N 2001/1427* (2013.01)

(56) References Cited

U.S. PATENT DOCUMENTS

| | | | | |
|---|---|---|---|---|
| 5,254,312 | A * | 10/1993 | Staebler | B01L 3/0293 422/501 |
| 5,893,842 | A * | 4/1999 | Imbert | A61M 5/5013 604/110 |
| 5,910,289 | A * | 6/1999 | Sagstetter | B01L 3/0293 422/512 |
| 7,153,386 | B2 * | 12/2006 | Sagstetter | B01L 3/0293 156/293 |
| 2009/0246085 | A1 * | 10/2009 | Watson | B01L 3/0293 422/400 |
| 2014/0162353 | A1 * | 6/2014 | Faulkner | G01N 1/10 435/309.1 |
| 2014/0329319 | A1 * | 11/2014 | Scott | B01L 3/0293 435/375 |

* cited by examiner

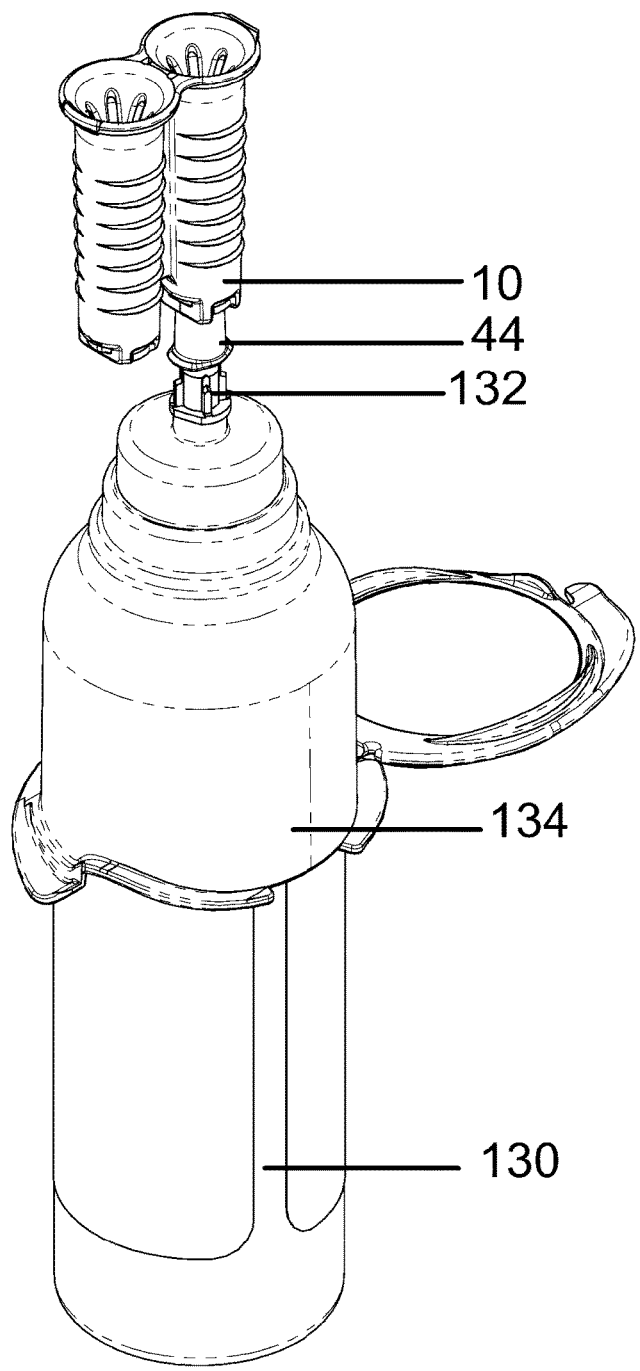
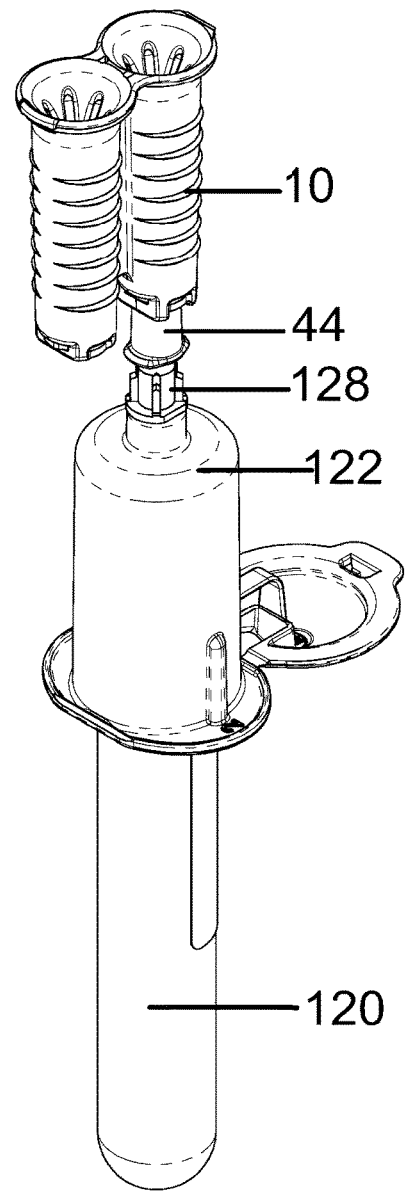
Figure 14
Figure 13

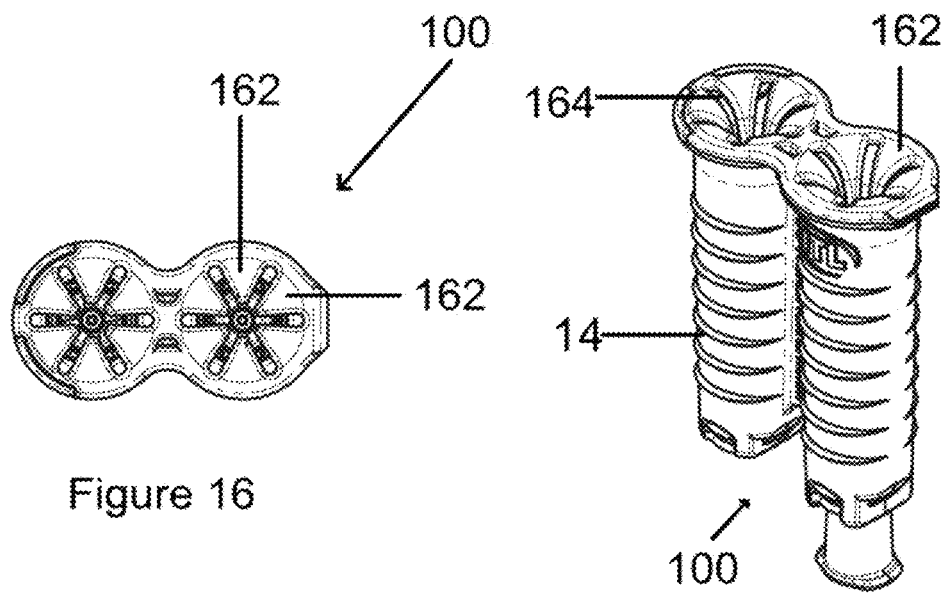
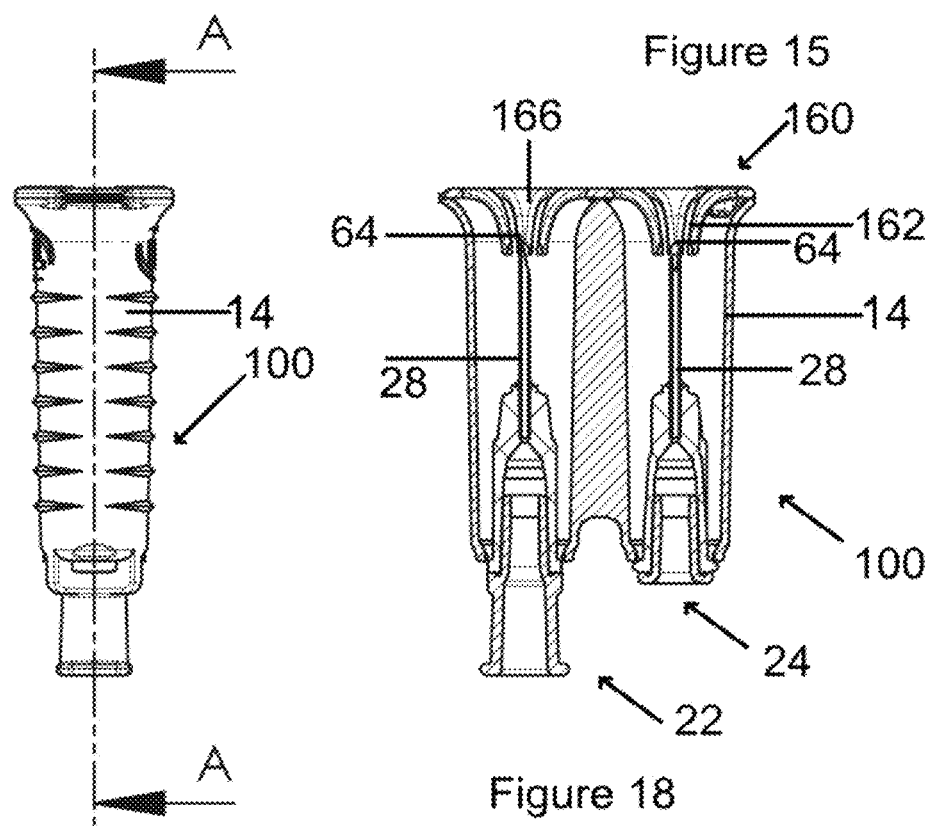

SEGMENT SAMPLER

FIELD OF INVENTION

This invention relates to tube segments that contain blood or blood products and more particularly to a sampling device for sampling fluid from tube segments. However, the invention is not limited to sampling of blood, blood products or other biological material and may be applied to sampling other materials.

BACKGROUND

Blood and blood products need to be tested after donation or further processing. Rather than testing a blood (or blood products) bag directly a relatively small sample may be held in a sealed tube that is cross-referenced to the actual product bag. Such sealed tubes are referred to as "blood Bag segments", "tube segments" or "blood segments". The term "tube segment" will be used in this specification and it is understood to mean a tube that contains a fluid and which is sealed at both ends.

Testing requires removal of some of the fluid in the tube, usually by passing a cannula into one end of the tube and stripping the tube with pliers to push fluid out of the tube. This method has various inconveniences and occupational hazards. Another method is to pass a cannula into one end of the tube segment and apply suction (either by using a syringe or an evacuated tube). Whilst the tubes are relatively flexible, this requires a reduction in volume of the tube or displacement of liquid by environmental fluid (such as air), without which fluid will not be withdrawn from the tube. The present invention aims to provide a device and method which aids withdrawal of fluid from tube segments.

SUMMARY OF THE INVENTION

In one broad form the invention provides a tube segment sampler for withdrawing a fluid sample from a tube segment, the sampler having a first tube piercing member having a first piercing part for piercing the tube segment at a first location and a second tube piercing member having a second piercing part for piercing the tube segment at a second location.

Preferably, the first and second locations are spaced from each other.

Preferably, the first tube piercing member is adapted to have at least a portion remain in the tube segment whilst a fluid sample is withdrawn.

Preferably, the second tube piercing member is adapted to have at least a portion remain in the tube segment whilst a fluid sample is withdrawn.

Preferably, the first tube piercing member is adapted for connection to a sample receiver or an adaptor for a sample receiver. Preferably, the first tube piercing member includes a first connection portion for connection to a sample receiver or an adaptor for a sample receiver.

Preferably, the first tube piercing member includes a first passageway that, in use, communicates the first connection portion with the interior of the tube segment.

Preferably, the second tube piercing member is adapted to allow environmental fluid (such as air) from the environment to enter the tube segment as fluid is withdrawn.

Preferably, the second tube piercing member defines a second passageway that, in use, communicates the environment with the interior of the tube segment. Preferably, the second passageway is internal of the second tube piercing member. Where the second tube piercing member remains in the tube segment whilst a fluid sample is withdrawn, the second passageway may also be defined between the second tube piercing member and the wall of the tube segment.

The second tube piercing member may be configured to create a second passageway through the wall of the tube segment but not remain in the tube segment whilst a fluid sample is withdrawn.

Where the second passageway is internal of the second tube piercing member the second tube piercing member may be adapted for connection to a sample receiver or an adaptor for a sample receiver, such that either the first or second piercing member may be connected to a sample receiver or an adaptor for a sample receiver. Preferably, the second tube piercing member includes a second connection portion for connection to a sample receiver or an adaptor for a sample receiver.

The first and second piercing members may be adapted to pierce a sidewall of the tube segment or an end portion of the tube segment. The tube segment may be heat sealed at its ends, with the sidewall of the tube segment flattened and heat sealed against itself to form an end. It is to be understood that reference to an end or an end portion of a tube segment may include a heat sealed end portion of the tube segment Preferably, the first tube piercing member is adapted for piercing one end of the tube segment.

Preferably, the second tube piercing member is adapted for piercing the other end of the tube segment.

A sample receiver or an adaptor for a sample receiver may include but is not limited to a syringe, an evacuated tube, a sampling bottle, sampling barrel or tube barrel holder.

As used hereinafter, reference to a sample receiver includes reference to an adaptor for a sample receiver.

In preferred embodiments, one or both of the first and second tube piercing members may comprise a hollow cannula.

In a preferred embodiment, the first and second tube piercing members comprise a luer fitting, more preferably a female luer fitting. However, a male luer fitting or any other fitting may be used.

Where the second tube piercing member comprises a luer fitting, preferably a plug or a cap is located in and/or on the luer fitting of the second tube piercing member.

A luer extension member maybe located on and/or in the luer fitting of the first tube piercing member.

Each of the first and second tube piercing members may be located within a respective elongate space open at one end and adapted to receive a tube segment. The respective tube piercing member may include an elongate cannula having an axis and extending along the elongate space with a pointed end facing the open end, whereby an end of a tube segment passed into the space from the open end may be impaled on the cannula.

In a preferred form the first and second tube piercing members each comprise a cannula mounted on a separate needle block, more preferably a metal cannula mounted on a plastic needle block. However, the cannula may be mounted in a mounting formed integrally with material defining all or part of the respective elongate space.

Preferably, the cannula has a free end and the free end is located within the elongate space spaced from the open end. The free end of the cannula forms the piercing part.

Preferably, the elongate space has a guide member located or mounted on or in the open end for guiding a tube segment onto the piercing part, the free end in the case of a cannula.

Preferably the guide member comprises a funnel shaped surface or surfaces.

In one embodiment, the guide member may include slots arranged radially about the funnel shaped surface or surfaces to define a series of arms or fingers. The sealed end of the tubing segment usually has flat portion with a width wider than the diameter of the tubing, but a thickness thinner than the diameter of the tubing. The radial slots serve to allow the fingers to flex outwards and allow the flat portion of the tubing to pass through the guide member while maintaining a minimum diameter to the guide member aperture. If desired in the un-deflected state the fingers may define an opening of a smaller size than the diameter of the tube segment, so that the fingers are deflected outwards and bear against the tube whilst the tube is inserted into the guide member.

Preferably, the guide member has an inner end remote from the open end.

On one embodiment, the piercing part, the free end in the case of a cannula, extends toward but not into the guide member. On another embodiment, the piercing part, the free end in the case of a cannula, extends into or is located in the passageway defined by the guide member.

In a preferred embodiment each elongate space may be defined by a generally tubular body having an opening at one end and a closed other end, the closed other end including an aperture for receiving a tube piercing member.

The tubular body and tube piercing member may include complementary structures to lock the tube piercing member received in the aperture. The complementary structures may include at least one protrusion on one of the tubular body and the tube piercing member and at least one recess or aperture on the other of the tubular body and the tube piercing member.

In a preferred form the tube segment sampler comprises two generally tubular bodies arranged side by side with a cannula mounted axially in each tubular body and extending toward an open end of the respective tubular body. A first cannula is in communication with a fitting for connection to a sample receiver and the other cannula is in communication with the ambient environment.

The invention also provides a method of removing a fluid sample from a sealed tube segment, comprising creating a first opening in the tube segment; creating a second opening in the tube segment and withdrawing fluid from the tube segment through the first opening member whilst allowing environmental fluid to pass into the tube segment via the second opening.

Preferably, the step of creating a first opening in the tube segment comprises creating a first opening in a first end of the tube segment.

Preferably, the step of creating a first opening in the tube segment comprises passing a cannula into the tube segment.

Preferably, the step of creating a second opening in the tube segment comprises passing a second cannula into the tube segment.

Preferably, the step of creating a second opening in the tube segment comprises creating a second opening in a second end of the tube segment.

Preferably, the step of creating a first opening in the tube segment comprises passing an end of the tube segment into the open end of a receptacle having a cannula mounted therein and impaling the end on the cannula.

Preferably, the step of creating a second opening in the tube segment comprises passing an end of the tube segment into the open end of a receptacle having a cannula mounted therein and impaling the end on the cannula.

Preferably, the fluid sample is removed from the tube segment via the first cannula.

Preferably, the second cannula remains in the tube segment whilst the fluid sample is removed.

For avoidance of any doubt, the term piercing is to be interpreted as the making of an opening in the tube segment by any means, whether by insertion of an object through the tube wall or by cutting the tube wall. This includes, but is not limited to, use of a cannula, a solid spike or a blade.

BRIEF DESCRIPTION OF THE DRAWINGS

FIG. 13 is a perspective view of the sampling device in use with an evacuated tube, with the tube segment omitted for clarity;

FIG. 14 is a perspective view of the sampling device in use with a sampling bottle, with the tube segment omitted for clarity.

FIG. 15 is a perspective view of the sampling device according to another embodiment of the invention.

FIG. 16 is a top view of the sampling device of FIG. 15;

FIG. 17 is a side view of the sampling device of FIG. 15;

FIG. 18 is a sectional view taken along line AA of FIG. 17;

DETAILED DESCRIPTION OF PREFERRED AND OTHER EMBODIMENTS

Figure 1:
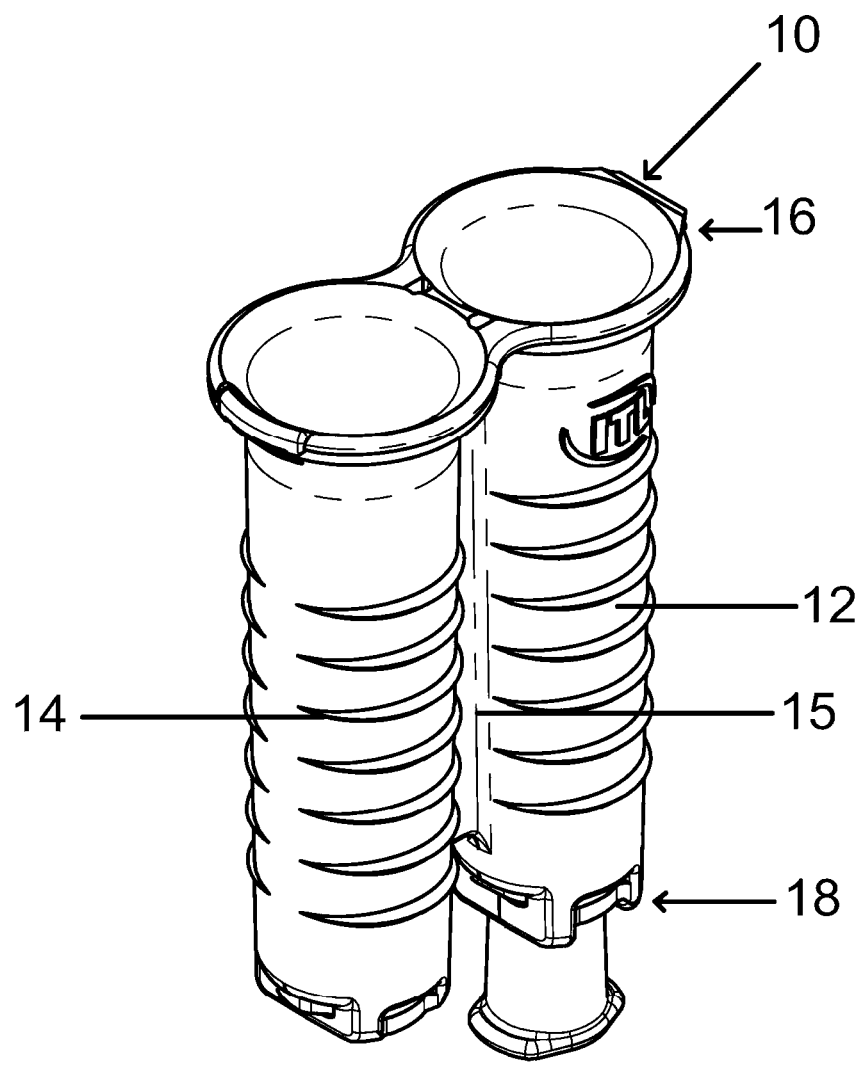
FIG. 1 is a perspective view from above of a tube segment sampling device according to an embodiment of the invention.
Figure 2:
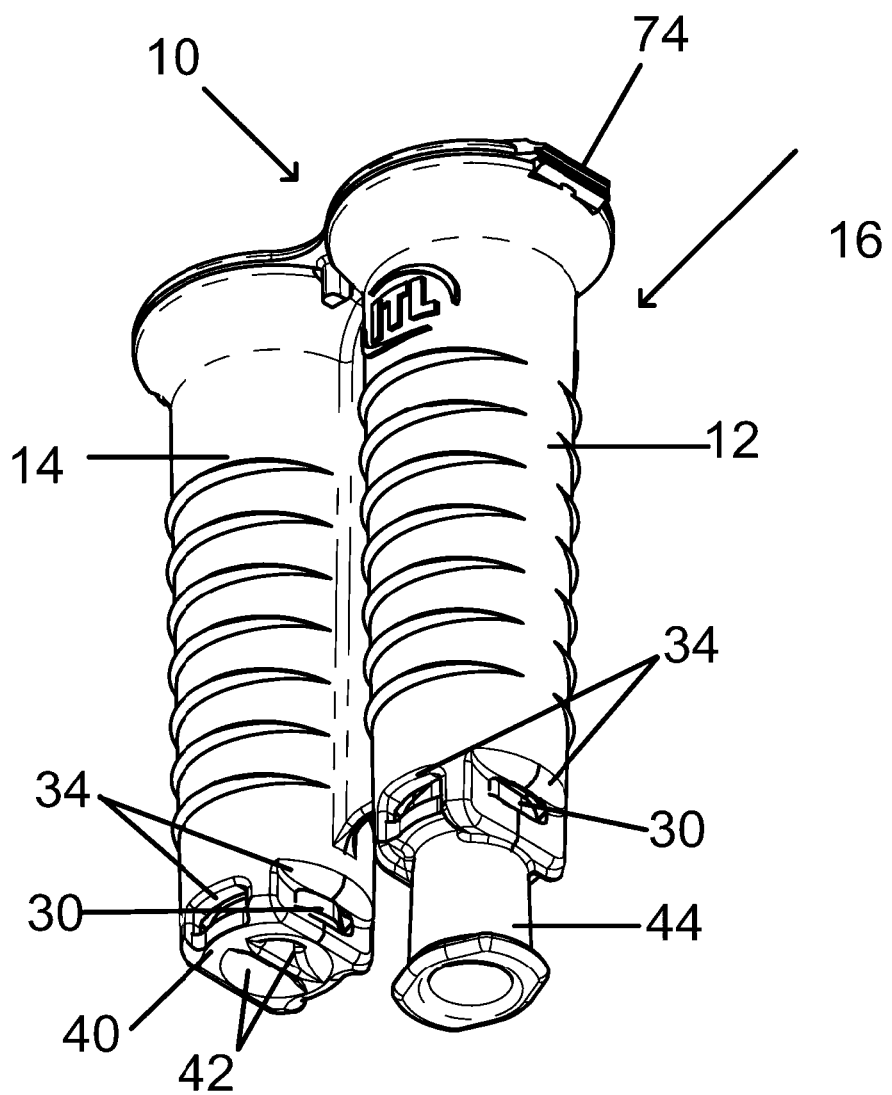
FIG. 2 is a perspective view from below of the sampling device of FIG. 1.
Figure 3:
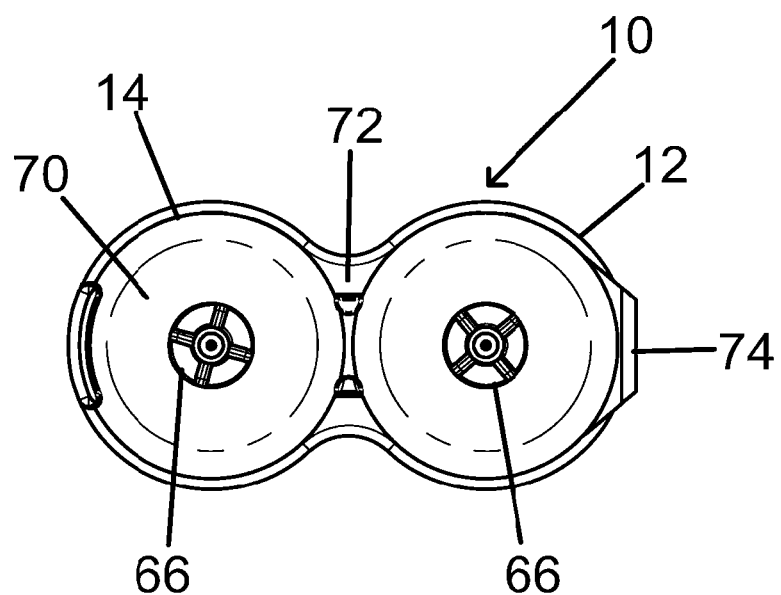
FIG. 3 is a top view of the sampling device of FIG. 1.
Figure 4:
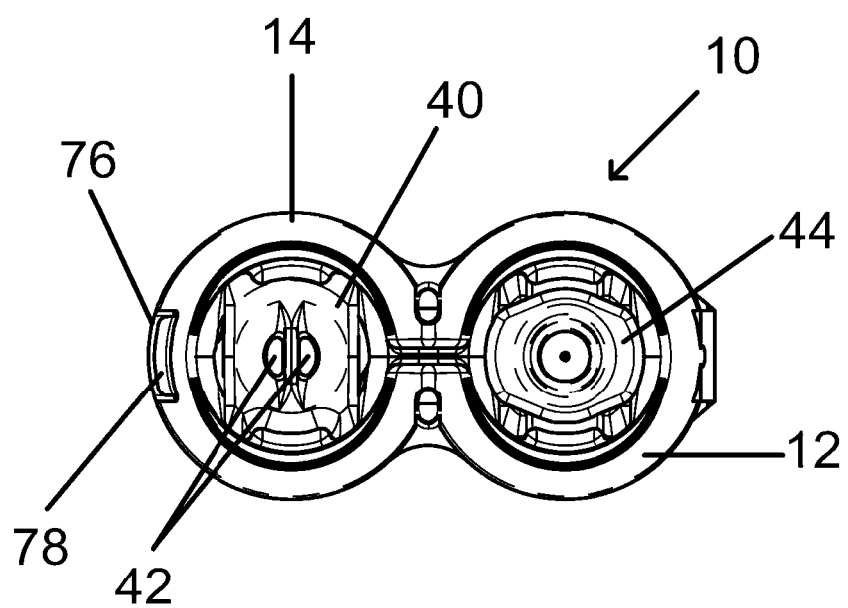
FIG. 4 is a bottom view of the sampling device of FIG. 1.
Figure 5:
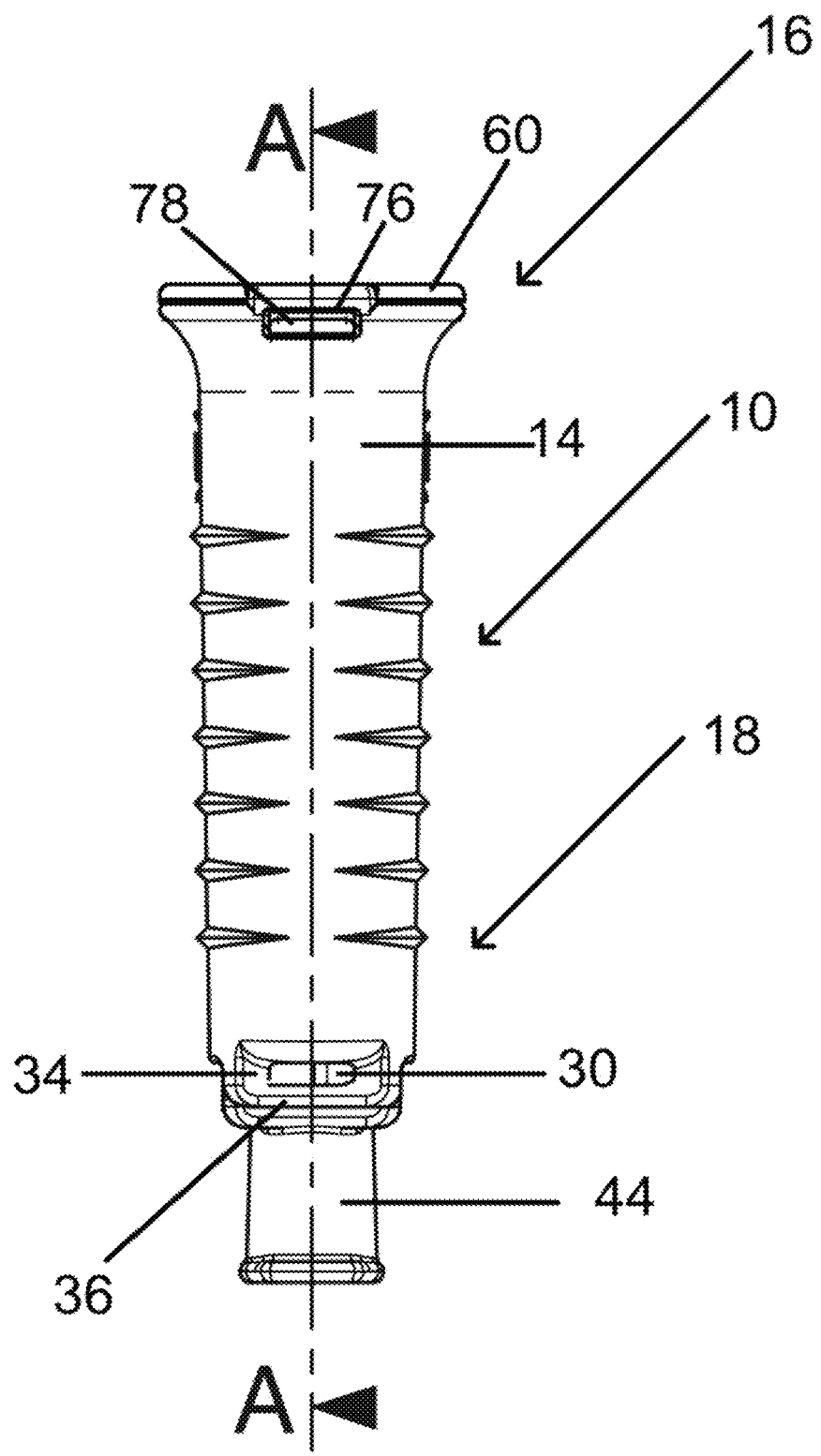
FIG. 5 is a side view of the sampling device of FIG. 1.
Figure 6:
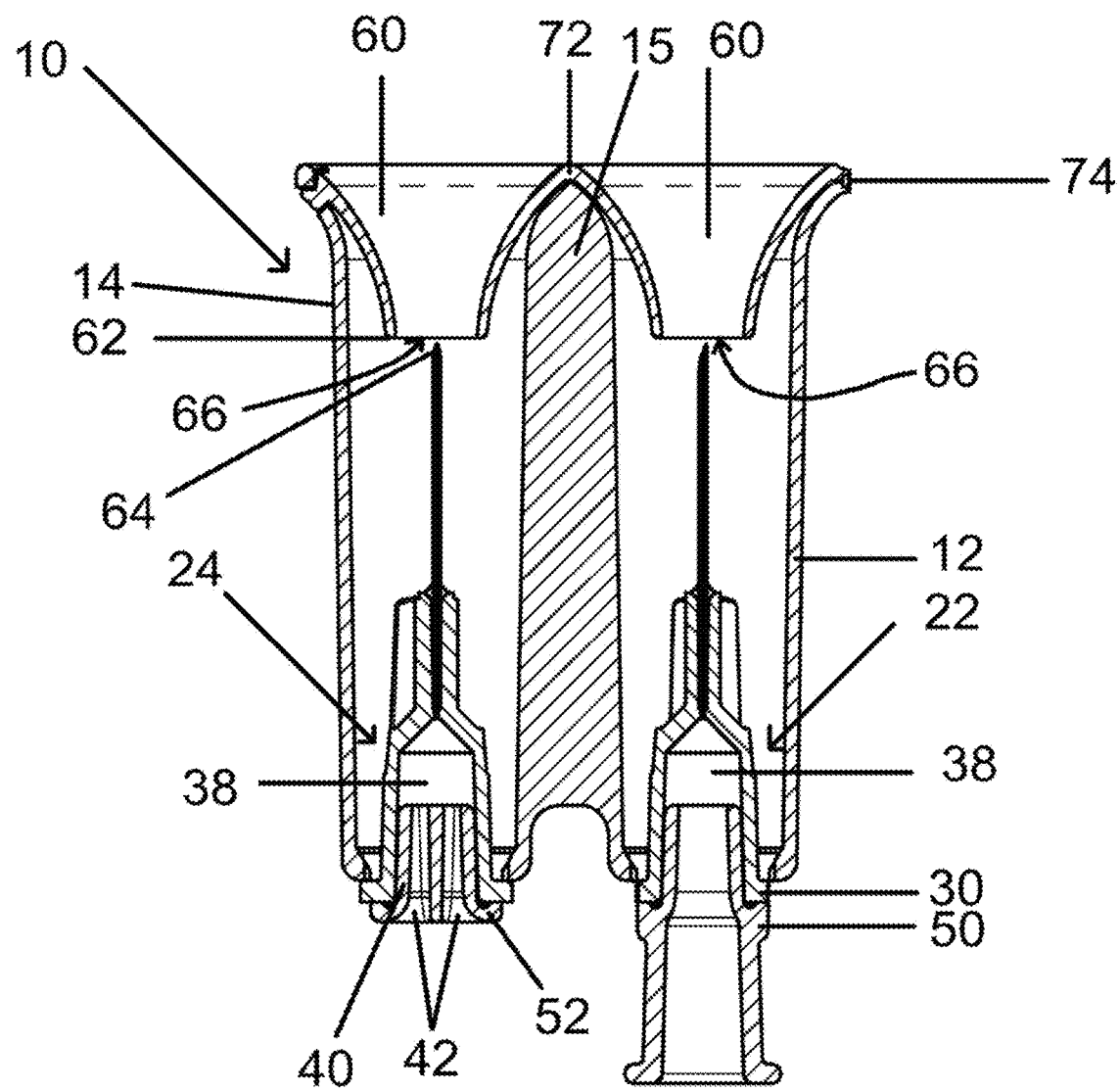
FIG. 6 is a sectional view taken along line AA of FIG. 5.
Figure 7:
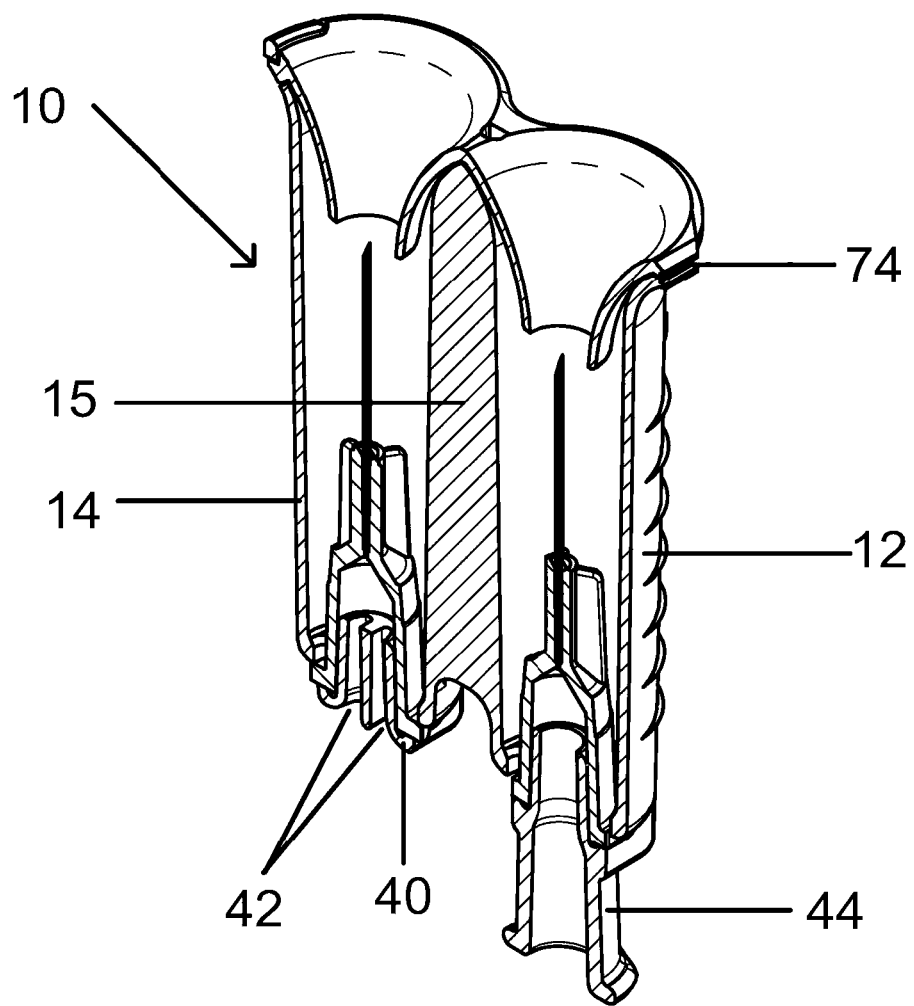
FIG. 7 is a perspective sectional view taken along line AA of FIG. 5.

Referring to the drawings there is shown a tube segment sampling device 10. The sampling device 10 comprises a unitary body having cylindrical or tubular portions 12 and 14 joined by web 15. Each portion 12 and 14 may be a separate body formed separately and subsequently joined together.

The two portions 12 and 14 are substantially identical. Each has an upper end 16 and a lower end 18. The lower ends 18 have an aperture 20 formed therein into which needle assemblies 22 and 24 are located. The needle assemblies 22 and 24 are identical and comprises a needle block 26 into which a cannula 28 is mounted.

The needle blocks 26 are generally cylindrical with an annular flange 30 at their lower end. The aperture 20 is smaller than the flange 30 but the lower end 18 has apertures 34 spaced in the wall defining/surrounding the aperture 20. The needle assemblies may be press fitted into the apertures 20, with legs 36 defining the apertures 34 deflecting to allow the flange to pass and then engage in the apertures 34, thereby securing the needle assembly in place. This arrangement is preferred but other arrangements such as an interference press fit may be used.

For manufacturing efficiency and cost, these needle assemblies 22 and 24 may be standard luer type needle assemblies. Accordingly, the lower end of each needle block 26 has a female luer fitting 38. The needle assemblies 22 and 24 do not need to be standard luer type needle assemblies. The needle assemblies 22 and 24 do not need to have a luer coupling (male or female) at their lower end.

The needle blocks 26 may be formed integrally with the respective portions 12 and 14, rather than being a separate component, with the cannulas being mounted directly in the unitary portions 12 and 14 and communicating with an appropriate opening.

The needle assembly 24 has a plug 40 inserted into the female luer fitting 38. The plug 40 includes one or more passageways 42 whereby air may pass through the needle block into the cannula. If formed integrally with the portion 14 it is not necessary to form a female luer fitting and the mounting for the cannula merely needs to provide a passageway to the outside environment.

Figure 11:
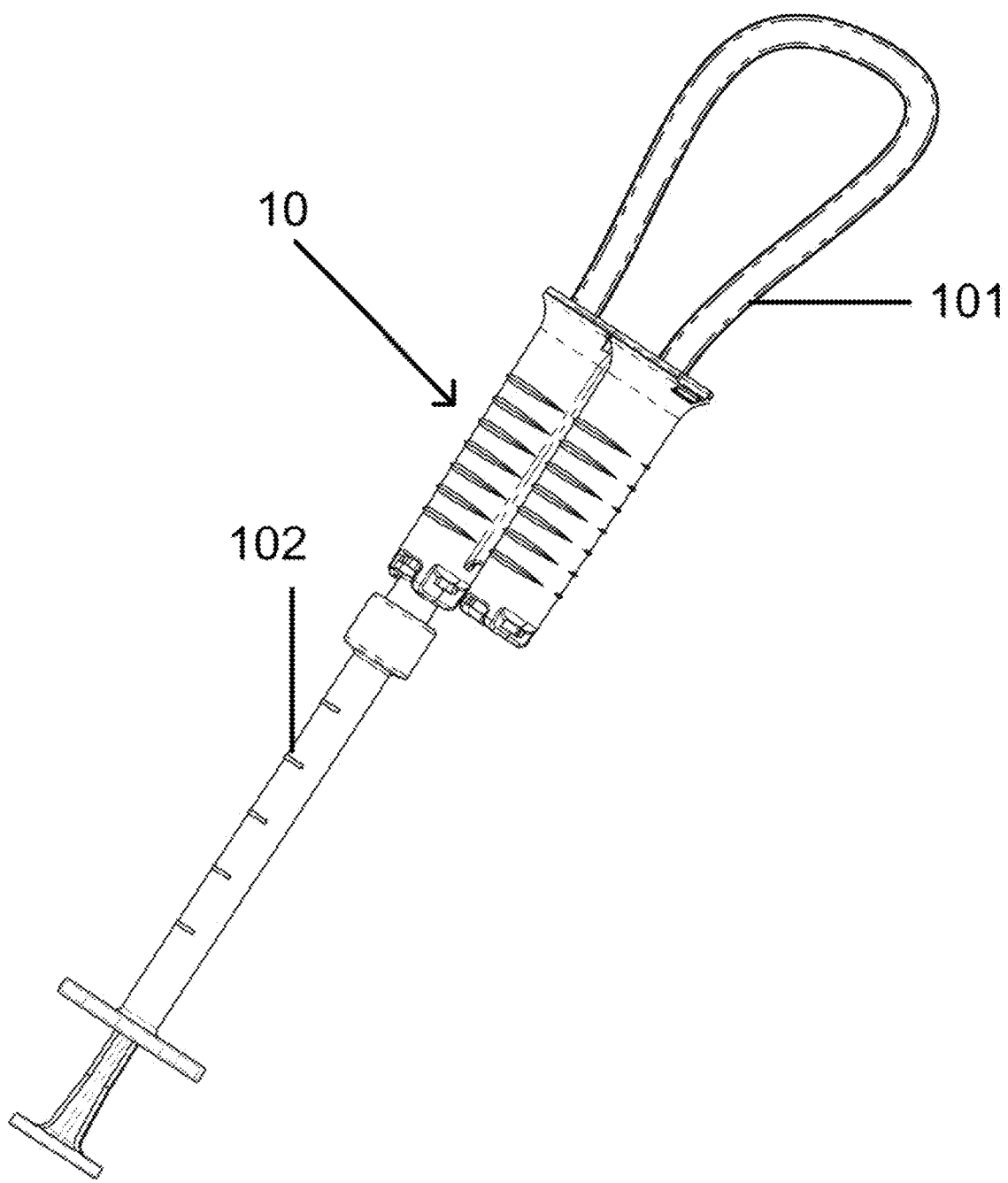
FIG. 11 is a perspective view of the sampling device in use with a tube segment and a syringe.

In the embodiment shown, the other needle assembly 22 is provided with a luer extension 44. The luer extension 44 has a male upper end 46 received in female luer fitting 38 and a female lower end 48 for receiving a male luer fitting of a sample receiver with a male luer fitting. Examples of a sample receiver with a male luer fitting include a syringe as in FIG. 11 or evacuated tubes or bottles as in FIGS. 13 and 14. If formed integrally with the portion 12 the cannula mounting may be formed to extend downwards in a similar manner with a female luer fitting at a similar location. Alternatively, the needle assembly 22 may be provided with a longer needle block.

The extension 44 is not critical but serves to provide a visual indication to a user as to where to connect the syringe or other sampling device. Without the extension the device 10 is substantially symmetrical and the user would need to inspect the end of the needle assemblies 22, 24 to determine which one to connect to.

In a similar manner, the plug 40 is not critical and may be omitted. Thus, the invention includes embodiments, which do not include either or both of the extension 44 and the plug 40.

Where the plug 40 is omitted and the second needle block 24 has a luer fitting the same as that on needle block 22 or extension 44 the user may connect a sample receiver to either of the portions 12 and 14.

Where both the extension 44 and the plug 40 are omitted the two portions 12 and 14 and associated needle assemblies are substantially identical.

If desired the extension 44 and/or the plug 40 may be locked in place by a flange 50 or 52 respectively received in openings 34. In that variant the opening 34 will be taller to accommodate both flanges.

The upper end 16 of each cylindrical portion 12 and 14 is provided with a funnel shaped guide member 60.

The lower end 62 of each guide member 60 ends above the free end 64 of the cannulas. The guide members 60 thus serve to limit access to the cannulas and aid in limiting needle stick injury.

Figure 12:
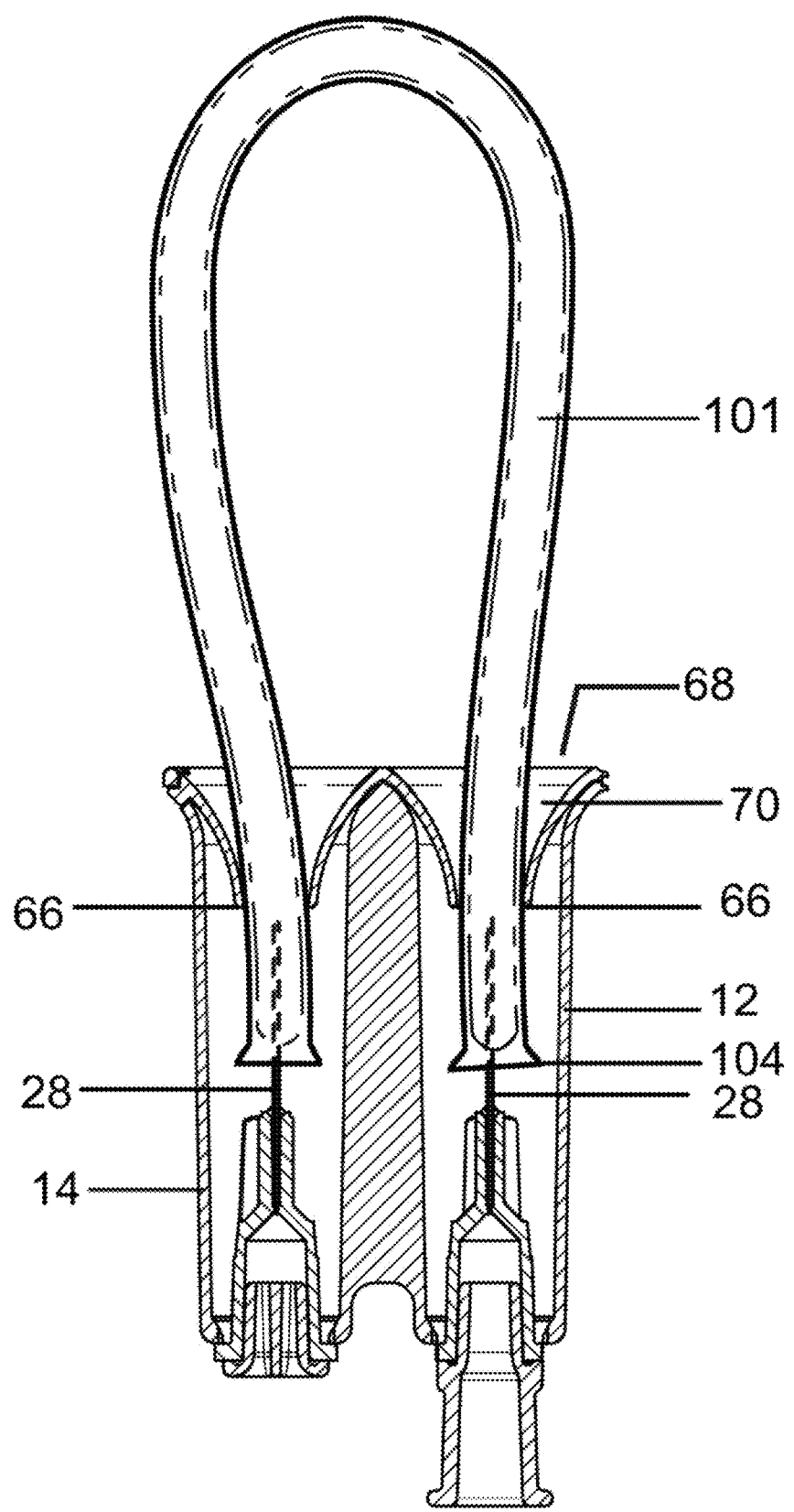
FIG. 12 is a sectional view similar to FIG. 2 but in use with a tube segment.

As best seen in FIG. 12 each guide member 60 has a lower aperture 66 that is of similar diameter to the tube segment 101 with which the device 10 is intended to be used. The upper end 68 of the guide member 60 is substantially larger and so the wall 70 of the guide member 60 serves to guide and centralise a tube segment over the respective cannula 28. The lower aperture 66 also holds the tube segment in position.

The two guide members 60 are preferably formed integrally with each other and with the cylindrical portions 12, 14. Accordingly, the two guide members 60 are connected to each other at 72 and to portion 12 at hinge 74. Portion 14 has aperture 76 into which re-entrant barb 78 engages. If desired the guide members may be formed separately from the cylindrical portions 12, 14 and/or from each other.

Whilst the preferred embodiment has each guide member 60 having a single continuous wall 70 extending inwards and downwards from the upper end 68, there may be a series of fingers extending downwards and inwards. Alternatively, there may be one or more axially extending slots in the wall 70 defining a series of fingers. FIGS. 13 to 18 show devices having guide members formed with fingers/slots.

If desired the guide members 60 may be omitted.

In use the user obtains a sampling device 10 and connects a sample receiver, such as a syringe 102 (see FIG. 11) or other sample receiver (see FIGS. 13 and 14) to the needle block 44 of portion 12. Either before or afterwards, the user takes a tube segment 101 and passes the ends 104 through a respective one of the apertures 66 and impales the ends 104 on the respective cannulas 28.

Where the sample receiver is a syringe the user withdraws the syringe plunger, so drawing a small amount of the fluid within the tube segment into the syringe body. Simultaneously air is drawn into the tube segment via plug 40 and cannula 28, thus allowing the fluid to more easily flow into the syringe body than otherwise. In a similar manner, when the sample receiver is an evacuated tube or bottle, as seen in FIGS. 13 and 14, on fluid connection of the evacuated tube or bottle with the interior of the tube segment, ambient air pressure drives air into the tube segment via plug 40 and fluid flows into the evacuated tube. It will be appreciated that when used with an evacuated sample receiver the tube segment needs to be impaled on the two cannulas 28 before connection of the sample receiver to the sampler 10.

The sampling device 10 may be used with devices other than a syringe, evacuated tube or bottle. When fitted with a standard female luer fitting any existing sampler with a male luer fitting may be used.

FIG. 13 shows the device 10 in use with an evacuated tube 120. A tube sampler 122 connects to the female luer fitting 48 via male luer fitting 128. The evacuated tube 120 is impaled on a downwardly extending cannula (not shown) that communicates with the male luer fitting 128.

FIG. 14 shows the device 10 in use with an evacuated sampling bottle 130. The evacuated sampling bottle 130 is impaled on a downwardly extending cannula (not shown) that communicates with male luer fitting 132 of adaptor cap 134. Male luer fitting 132 connects to female fitting 48. It will be noted that the guide members of the device 10 shown in FIGS. 13 and 14 have slots defining series of fingers.

FIGS. 15 to 18 show a device 100 that is otherwise identical to the device of FIGS. 1 to 14 except for the arrangement of its guide members. The common components are not numbered or utilise the same numbers.

The device 100 comprises a unitary body having cylindrical or tubular portions 12 and 14 joined by web 15 and carrying needle assemblies 22 and 24 into each of which into a cannula 28 is mounted.

The upper end 16 of each cylindrical portion 12 and 14 is provided with a funnel shaped guide member 160. In this embodiment each guide member 160 is formed of six equal fingers 162, separated by slots 164. As best seen in FIG. 18, the free ends 64 of the two cannulas 28 extend into the guide passageway 166 defined by the guide fingers 162.

The preferred embodiments shown are two tubular bodies joined by a web, albeit integrally formed. If desired the web may be omitted and the two bodies left as separate components or attached (temporarily or permanently) to each other by other structures.

Figure 8:
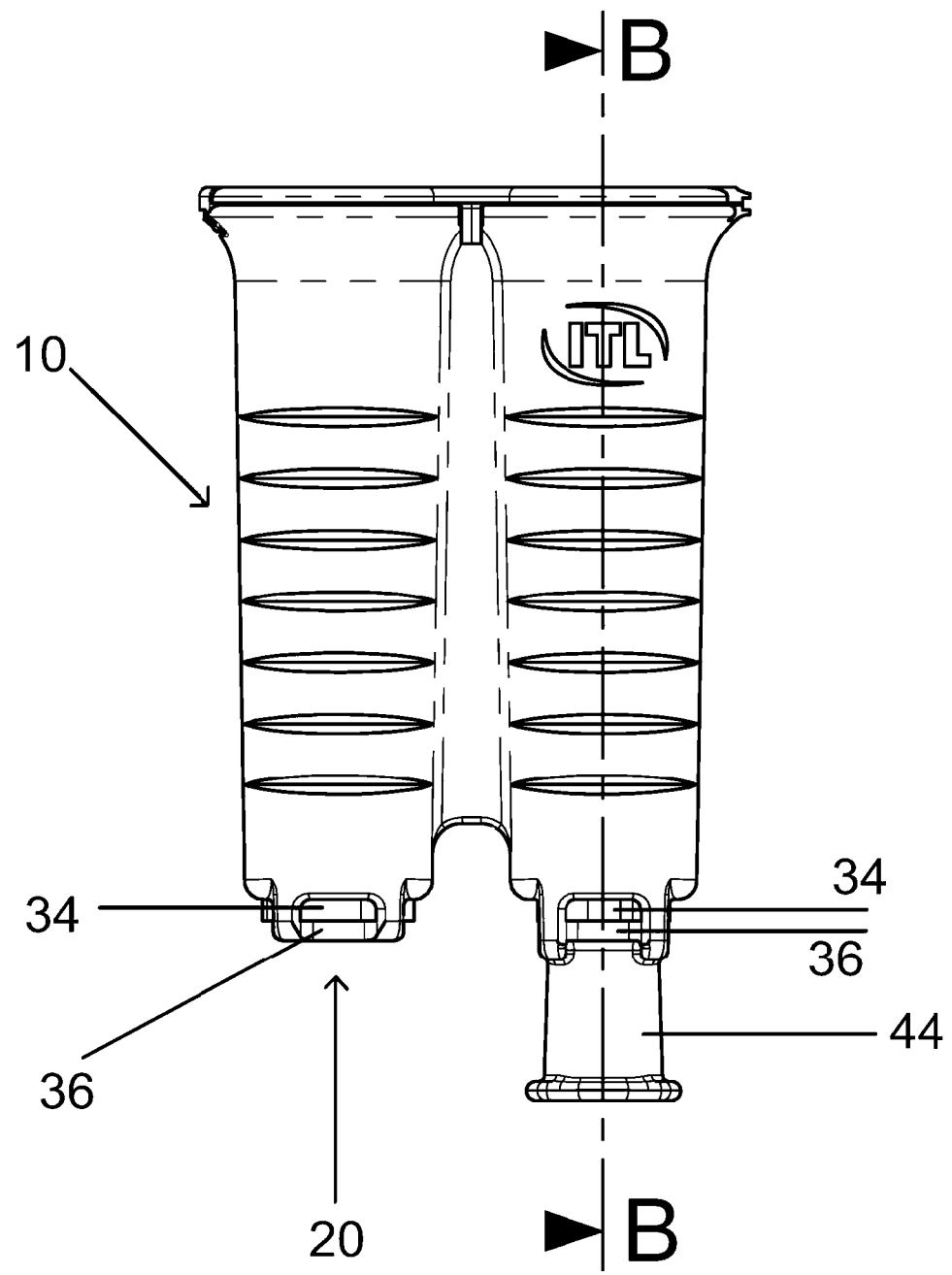
FIG. 8 is a front view of the sampling device of FIG. 1.
Figure 9:
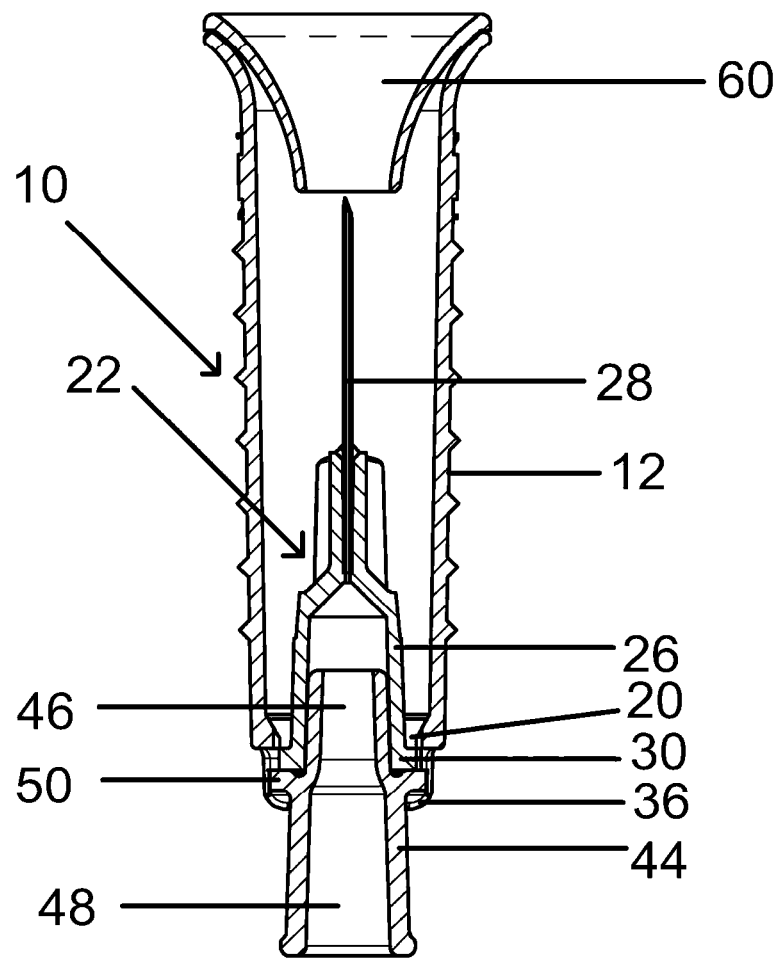
FIG. 9 is a sectional view taken along line BB of FIG. 8.
Figure 10:
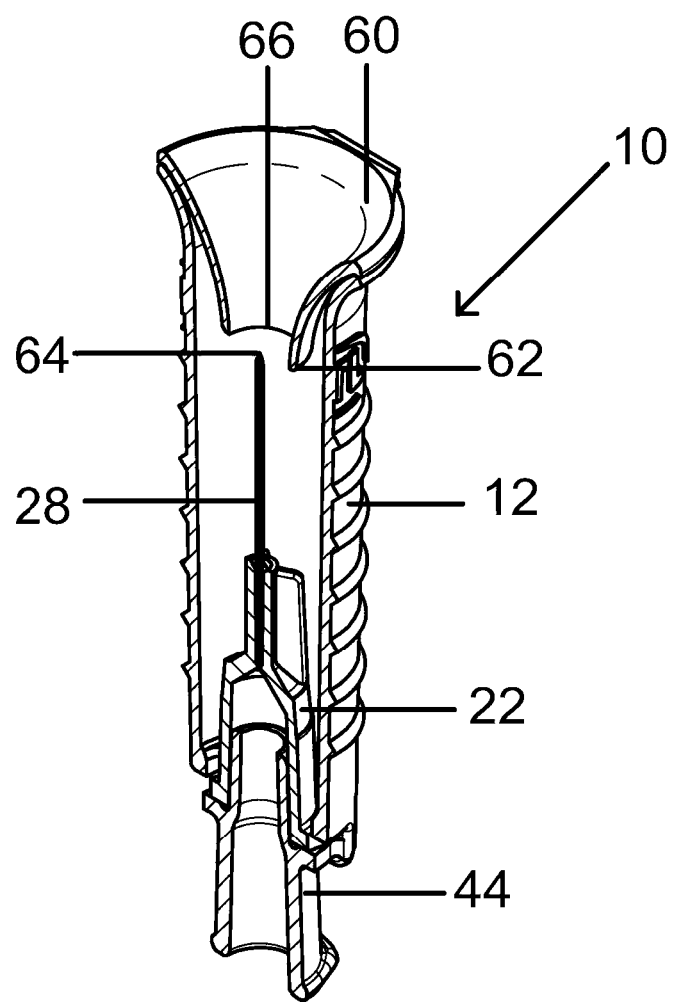
FIG. 10 is a perspective sectional view taken along line BB of FIG. 8.

The two tubular bodies may be formed integrally with a FIG. 8 like cross section. The cross sections of each tubular space in which the piercing members are located does not need to be circular. The central wall between the tubular spaces may be omitted so as to a single space in which the two piercing members extend, with separate openings for each piercing member.

Whilst the preferred embodiments have the two piercing members being elongate cannulas extending is spaced apart and parallel manner this is not essential and they may extend in other arrangements, such as back to back in a single tubular body with the pointed ends at opposite ends of single tubular body.

Whilst the preferred embodiment has two substantially identical two tubular bodies that receive substantially identical piercing members, it will be appreciated that one of the piercing members merely needs to pierce, cut or otherwise create an opening in the tube segment to allow air to enter. As such one of the piercing elements may be a simple spike or blade that penetrates or cuts the tube wall.

Unless the context clearly requires otherwise, throughout the description and any claims the words "comprise", "comprising", and the like are to be construed in an inclusive sense as opposed to an exclusive or exhaustive sense; that is to say, in the sense of "including, but not limited to".

The features of the invention described or mentioned in this document may be combined in any combination of features where features are not mutually exclusive.

It will be apparent to those skilled in the art that many obvious modifications and variations may be made to the embodiments described herein without departing from the spirit or scope of the invention.

The claims defining the invention are as follows:

1. An integrated tube segment sampler system for withdrawing a fluid sample from an elongate tube segment having at least one wall defining a sealed interior, the sampler having:
    a longitudinally extending first tube piercing member having a first piercing part for piercing and creating a first opening in the at least one wall and
    a longitudinally extending second tube piercing member having a second piercing part for piercing and creating a second opening in the at least one wall;
    at least one shield body that defines at least one shielded space, the first and second tube piercing parts located within the at least one shielded space;
    said at least one shield body including:
        a first tube segment receiving opening sized and located to allow a first end of the tube segment to pass into the shielded space and for the first end to be impaled on the first tube piercing part, with the first tube piercing member extending longitudinally through the first end and longitudinally within the tube segment;
        the first tube piercing member defines at least part of a first passageway internal of the first tube piercing member that, in use, communicates with the interior of the tube segment;
        the first passageway being in fluid communication with a first connection portion adapted for connection to a sample receiver or an adaptor for a sample receiver;
        a second tube segment receiving opening sized and located to allow a second end of the tube segment to pass into the shielded space and for the second end to be impaled on the second tube piercing part whilst the tube segment is impaled on the first tube piercing part;
        with the second tube piercing member extending longitudinally through the second end and longitudinally within the tube segment and creating a second passageway that, in use, communicates the environment with the interior of the tube segment.

2. A tube segment sampler system as claimed in claim 1 wherein the at least one shielded space comprises one generally tubular space.

3. A tube segment sampler system as claimed in claim 1 wherein the at least one shield body defines two shielded spaces.

4. A tube segment sampler system as claimed in claim 3 comprising two shield bodies, each defining a one of the two shielded spaces.

5. A tube segment sampler system as claimed in claim 4 including at least one guide member for guiding at least one of the first and second ends of the tube segment onto the respective tube piercing member.

6. A tube segment sampler system as claimed in claim 4 wherein said two shield bodies are attached to each other.

7. A tube segment sampler system as claimed in claim 4 wherein the two shield bodies are formed as a unitary member.

8. A tube segment sampler system as claimed in claim 7 wherein the two shielded spaces are arranged side by side.

9. A tube segment sampler system as claimed in claim 4 wherein the at least one shield body and the first tube piercing member include complementary lock structure to lock the first tube piercing member to the at least one shield body.

10. A tube segment sampler system as claimed in claim 9 wherein the complementary structures include at least one protrusion on one of the tubular body and the first tube piercing member and at least one recess or aperture on the other of the tubular body and the first tube piercing member.

11. A tube segment sampler system as claimed in claim 4 wherein the first and second tube piercing members are arranged generally parallel to each other.

12. A tube segment sampler system as claimed in claim 4 wherein the first and second tube piercing members each have a free end and a base end, the first and second tube piercing members each extending from the base end to the free end in the same direction as the other.

13. A tube segment sampler system as claimed in claim 4 wherein the first and second tube piercing members each have a free end and a base end, the first and second tube piercing members each extending from the base end to the free end in the opposite direction to the other.

14. A tube segment sampler system as claimed in claim 4 wherein at least one of the first and second tube piercing members comprises a cannula.

15. A tube segment sampler system as claimed in claim 4 wherein the second tube piercing member includes a second connection portion for connection to a sample receiver or an adaptor for a sample receiver.

16. A tube segment sampler system as claimed in claim 4 wherein the second passageway is internal of the second tube piercing member.

17. A method of removing a fluid sample from an elongate sealed tube segment having first and second ends, comprising:
creating a first opening in the tube segment by piercing the first end with a first tube piercing member having a first internal passageway, the first tube piercing member extending longitudinally through the first end and longitudinally within the tube segment;
creating a second opening in the tube segment by piercing the second end with a second tube piercing member, the second tube piercing member extending longitudinally through the second end and longitudinally within the tube segment, the second opening communicating the environment with the interior of the tube segment;
connecting a sample receiver having a sample receiver interior to be in fluid communication with the first passageway to provide a transfer passageway into the interior that is not exposed to the outside environment;
transferring fluid from the tube segment through the first opening member and into the sample receiver interior via the transfer passageway due to a pressure difference between the sealed interior and the sample receiver interior, the sample receiver interior being at a lower pressure than the environment, whilst simultaneously allowing environmental fluid to pass into the tube segment via the second opening.

18. A method of removing a fluid sample from a sealed tube segment comprising providing an integrated tube segment sampler having:
a longitudinally extending first tube piercing member having a first piercing part for piercing and creating a first opening in the at least one wall and
a longitudinally extending second tube piercing member having a second piercing part for piercing and creating a second opening in the at least one wall;
at least one shield body that defines at least one shielded space, at least one of the first and second tube piercing parts located within the at least one shielded space;
said at least one shield body including:
a first tube segment receiving opening sized and located to allow a first end of the tube segment to pass into the shielded space and for the first end to be impaled on the first tube piercing part, with the first tube piercing member extending longitudinally through the first end and longitudinally within the tube segment;
the first tube piercing member defines at least part of a first passageway internal of the first tube piercing member that, in use, communicates with the interior of the tube segment;
the first passageway being in fluid communication with a first connection portion adapted for connection to a sample receiver or an adaptor for a sample receiver;
a second tube segment receiving opening sized and located to allow a second end of the tube segment to pass into the shielded space and for the second end to be impaled on the second tube piercing part whilst the tube segment is impaled on the first tube piercing part;
with the second tube piercing member extending longitudinally through the second end and longitudinally within the tube segment and creating a second passageway that, in use, communicates the environment with the interior of the tube segment; and
creating a first opening in the tube segment by piercing the first end with the first tube piercing member, the first tube piercing member extending longitudinally through the first end and longitudinally within the tube segment;
creating a second opening in the tube segment by piercing the second end with a second tube piercing member, the second tube piercing member extending longitudinally through the second end and longitudinally within the tube segment, the second opening communicating the environment with the interior of the tube segment;
connecting a sample receiver having a sample receiver interior to be in fluid communication with the first passageway to provide a transfer passageway into the interior that is not exposed to the outside environment;
applying a pressure difference between the sealed interior and the sample receiver interior, the sample receiver interior being at a lower pressure than the environment so as to transfer fluid from the tube segment through the first opening and into the sample receiver interior via the transfer passageway due to, whilst simultaneously allowing environmental fluid to pass into the tube segment via the second opening.

19. A method of removing a fluid sample from a sealed tube segment as claimed in claim 18 wherein the sample receiver is an evacuated tube or bottle and the step of applying a pressure difference comprises connecting the sample receiver interior to be in fluid communication with the first passageway.

20. A method of removing a fluid sample from a sealed tube segment as claimed in claim 18 wherein the sample receiver is a syringe having a plunger movable within the sample receiver interior and the step of applying a pressure difference comprises moving the plunger to increase volume of the sample receiver interior.

21. A method of removing a fluid sample from a sealed tube segment as claimed in claim 20 wherein the step of connecting a sample receiver occurs before the step of creating a second opening.

* * * * *